(12) United States Patent
Cohen et al.

(10) Patent No.: US 11,123,004 B2
(45) Date of Patent: Sep. 21, 2021

(54) ELECTROPHYSIOLOGICAL RIPPLE MAPPING VISUALIZATION METHOD

(71) Applicant: BIOSENSE WEBSTER (ISRAEL) LTD., Yokneam (IL)

(72) Inventors: Assaf Cohen, Kiryat Bialik (IL); Goren Cohn, Haifa (IL); Ido Ilan, Yoqneam (IL); Aharon Turgeman, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 182 days.

(21) Appl. No.: 16/228,426

(22) Filed: Dec. 20, 2018

(65) Prior Publication Data

US 2020/0196890 A1    Jun. 25, 2020

(51) Int. Cl.
| | |
|---|---|
| A61B 5/04 | (2006.01) |
| A61B 5/0402 | (2006.01) |
| A61B 5/044 | (2006.01) |
| A61B 5/042 | (2006.01) |
| A61B 5/341 | (2021.01) |
| A61B 5/283 | (2021.01) |
| A61B 5/318 | (2021.01) |
| A61B 5/339 | (2021.01) |

(52) U.S. Cl.
CPC .............. *A61B 5/341* (2021.01); *A61B 5/283* (2021.01); *A61B 5/318* (2021.01); *A61B 5/339* (2021.01)

(58) Field of Classification Search
CPC ... A61B 5/04011; A61B 5/0402; A61B 5/042; A61B 5/044

USPC ......................................................... 600/512
See application file for complete search history.

(56) References Cited

U.S. PATENT DOCUMENTS

| | | |
|---|---|---|
| 2007/0232949 A1 | 10/2007 | Saksena |
| 2007/0299351 A1 | 12/2007 | Harlev et al. |
| 2010/0268059 A1 | 10/2010 | Ryu et al. |
| 2014/0081114 A1 | 3/2014 | Shachar et al. |
| 2017/0049348 A1 | 2/2017 | Deno et al. |
| 2017/0281031 A1* | 10/2017 | Houben ............... A61B 5/0036 |

OTHER PUBLICATIONS

European Search Report for corresponding EPA No. 19218127.9 dated Apr. 29, 2020.
Linton et al., "Cardiac ripple mapping: A novel three-dimensional visualization method for use with electroanatomic mapping of cardiac arrhythmias", Heart Rhythm, vol. 6, No. 12, pp. 1754-1762, Dec. 1, 2009.
Katritsis et al., "Arrhythmia Mechanisms Revealed by Rippling Mapping", Arrhythmia & Electrophysiology Review, vol. 7, No. 4, p. 1, Jan. 1, 2018.

\* cited by examiner

*Primary Examiner* — Erin M Piateski

(57) ABSTRACT

A method includes receiving an anatomical map of at least a portion of a heart. Positions and respective electrocardiogram (ECG) signal amplitudes measured at the positions are received for at least a region of the anatomical map. The ECG signal amplitudes are interpolated to derive a surface representation of the ECG signal amplitudes over the region. The surface representation of the ECG signal amplitudes is presented overlaid on the anatomical map.

10 Claims, 2 Drawing Sheets

ELECTROPHYSIOLOGICAL RIPPLE MAPPING VISUALIZATION METHOD

FIELD OF THE INVENTION

The present invention relates generally to electrophysiological mapping, and particularly to visualization of cardiac electrophysiological maps.

BACKGROUND OF THE INVENTION

Electrophysiological (EP) cardiac mapping may use visualizations methods previously proposed in the patent literature, to ease an interpretation of an EP map. For example, 2017/0049348 describes a method for determining EP properties of cardiac tissue in order classify an arrhythmia. An eccentricity parameter reflecting the uniformity of a local conduction velocity, and divergence and curl-like sums or closed path integral parameters associated with the local velocity vectors are provided, and a rhythm classification responsive to catheter movement is displayed, thereby facilitating identification of types and causes of arrhythmia disorders. In an embodiment, conduction velocity vector maps are coupled with local activation time (LAT) maps. Generally, the display is updated immediately following each local depolarization and persisting or gradually fading out until the next local depolarization. Finally, some or all isochrones may be displayed as curved lines on the cardiac surface, for instance at specific intervals since the start of depolarization. This reduces visual clutter and allows a more interpretable superposition of conduction velocity arrows.

As another example, U.S. Patent Application Publication 2010/0268059 describes a method that includes accessing cardiac information acquired via a catheter located at various positions in a venous network of a heart of a patient. The cardiac information comprises position information, electrical information and mechanical information. The method maps local electrical activation times to anatomic positions to generate an electrical activation time map. The method maps local mechanical activation times to anatomic positions to generate a mechanical activation time map. The method further generates an electromechanical delay map by subtracting local electrical activation times from corresponding local mechanical activation times, and renders at least the electromechanical delay map to a display.

SUMMARY OF THE INVENTION

An embodiment of the present invention provides a method including receiving an anatomical map of at least a portion of a heart. Positions and respective electrocardiogram (ECG) signal amplitudes measured at the positions are received for at least a region of the anatomical map. The ECG signal amplitudes are interpolated to derive a surface representation of the ECG signal amplitudes over the region. The surface representation of the ECG signal amplitudes is presented overlaid on the anatomical map.

In some embodiments, presenting the surface representation includes visualizing respective values of the surface representation as topographical heights above the anatomical map.

In some embodiments, presenting the surface representation includes presenting a semi-transparent surface that retains the anatomical map visible.

In an embodiment, interpolating the ECG signal amplitudes includes forming a shape including the interpolated and measured ECG amplitude values.

In some embodiments, the anatomical map presents Local Activation Times (LAT).

There is additionally provided, in accordance with an embodiment of the present invention, a system including a memory and a processor. The memory is configured to store an anatomical map of at least a portion of a heart, and to store, for at least a region of the anatomical map, positions and respective electrocardiogram (ECG) signal amplitudes measured at the positions. The processor is configured to interpolate the ECG signal amplitudes to derive a surface representation of the ECG signal amplitudes over the region, and present the surface representation of the ECG signal amplitudes overlaid on the anatomical map.

The present invention will be more fully understood from the following detailed description of the embodiments thereof, taken together with the drawings in which:

DETAILED DESCRIPTION OF EMBODIMENTS

Overview

In order to characterize cardiac electrophysiological (EP) abnormalities of a patient, a catheter-based EP mapping system may be used for generating an EP map of least part of the heart of the patient, such as an EP map of a cardiac chamber. In a typical catheter-based EP mapping procedure, a distal end of a catheter, which comprises sensing-electrodes, is inserted into the heart to sense EP signals. As a physician operating the system moves the distal end inside the heart, the EP mapping system acquires EP signals at various cardiac locations, as well as the respective positions of the distal end. Based on these acquired signals, a processor of the mapping system generates the required EP map.

In some cases, the processor of the EP mapping system presents the measured EP map overlaid on a heart anatomy visualized by, for example, a volume (3D) rendering of at least a portion of the heart. Such an EP overlaid rendering may be very useful in diagnosing cardiac irregularities. For example, ECG "spikes" overlaid on an anatomical map may be used, where the height of the spikes gives a measure of the ECG signal amplitude at the spike position. The spike representation may indicate an anomalous conduction path causing an arrhythmia.

However, this kind of visualization often tends to be too coarse and/or hides other features of diagnostic value. Moreover, such spikes only give a value of the signal at the given position, not in any intermediate positions, causing discontinuities in visualization, and furthermore the spikes may hide map details beneath or behind the spikes.

Embodiments of the present invention that are described hereinafter use a processor to interpolate between measured values of the ECG signal at points near a selected location, and represent these interpolated values as topographical heights above the 3D rendering. The topographical heights are connected graphically to give a 3D surface referred to as a "sail," having a continuous ripple, instead of a collection of spikes. In an embodiment, the "sails" are made semi-transparent in order not to hide details.

Typically, the processor is programmed in software containing a particular algorithm that enables the processor to conduct each of the processor related steps and functions outlined above.

The disclosed visualization technique to overlay interpolated ECG ripples, that may be semi-transparent, on 3D cardiac anatomy, may improve the diagnostic value of catheter-based EP mapping procedures.

System Description

Figure 1:
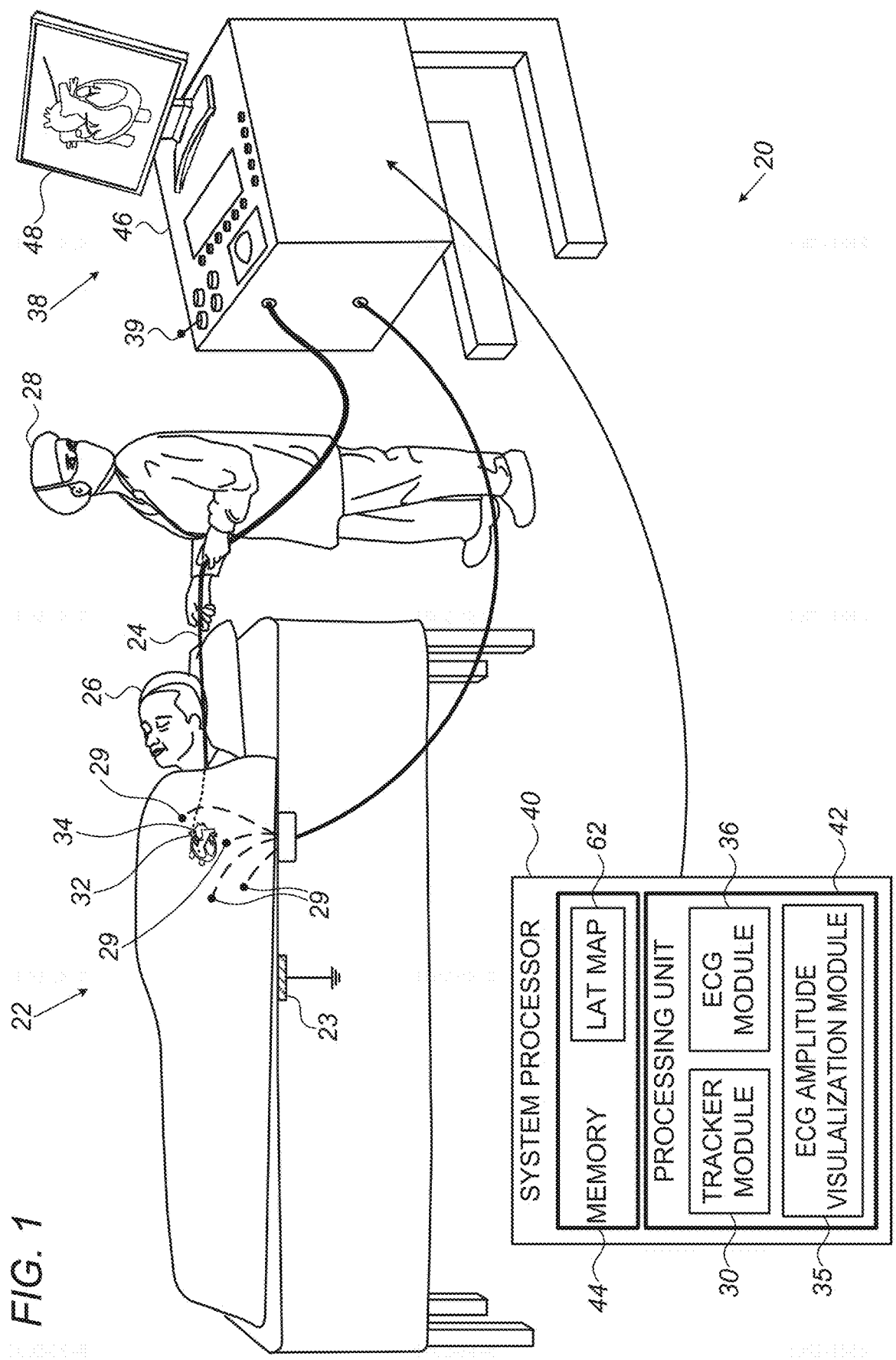
FIG. 1 is a schematic, pictorial illustration of a cardiac three-dimensional (3D) navigation and electrophysiological (EP) signal analysis system, in accordance with an embodiment of the present invention.

FIG. 1 is a schematic, pictorial illustration of a cardiac three-dimensional (3D) navigation and electrophysiological (EP) signal analysis system 20, in accordance with an embodiment of the present invention. System 20 may be configured to analyze substantially any physiological parameter or combinations of such parameters. In the description herein, by way of example, the signals analyzed are assumed to be intra-cardiac and/or extra-cardiac (body surface) electrocardiogram (ECG) potential-time relationships. In order to fully characterize such relationships, a processor 40 uses the ECG signals to produce an EP map, such as a local activation time (LAT) map. A method for generating an LAT map is described in U.S. Pat. No. 9,050,011, whose disclosure in fully incorporated herein by reference.

In the context of this disclosure, the term "anatomical map" refers to a map that models the 3D shape of at least a portion of the heart, and may have one or more parameters overlaid thereon. An EP map is one special case of an anatomical map, in which one or more electrophysiological parameters are overlaid. A LAT map is an example of an EP map, and thus also regarded as a type of anatomical map.

FIG. 1 shows an investigative procedure wherein system 20 measures actual electrical activity of a heart 34, using a probe 24. Typically, probe 24 comprises a catheter which is inserted into the body of patient 26 during a mapping procedure performed by a physician 28 using system 20. A distal end 32 of probe 24 is assumed to have electrodes 22. During the procedure patient 26 is assumed to be attached to a grounding electrode 23. In addition, electrodes 29 are assumed to be attached to the skin of patient 26, in the region of heart 34. In an embodiment, probe 24 acquires local intra-cardiac ECG as the probe moves over a portion of the heart chamber. At these instances, probe 24 location is recorded as well. The measured signals are used, as noted above and among other usages, to create an LAT map of at least part of the wall tissue of heart 34 of a patient 26.

System 20 is controlled by a system processor 40, comprising a processing unit 42 communicating with a memory 44. In some embodiments, a memory 44, which is included in system processor 40, stores an LAT and/or ECG map 62 of at least part of wall tissue of heart 34 of patient 26. Processor 40 is typically mounted in a console 46, which comprises operating controls 38, typically including a pointing device 39 such as a mouse or trackball, that physician 28 uses to interact with the processor.

Processor 40 (specifically processing unit 42) runs software, comprising a probe tracker module 30, an ECG module 36, and an ECG amplitude visualization module 35, used for visualizing ECG amplitudes over a 3D rendering of a portion of heart 26 anatomy (i.e., in the form of "sails"), as described above and described in further detail below. ECG module 36 is coupled to receive actual electrical signals from electrodes 22 and electrodes 29. The module is configured to analyze the actual signals and may present the results of the analysis in a standard ECG format, typically a graphical representation moving with time, on display 48.

Probe tracker module 30 typically tracks the location of distal end 32 of probe 24 within the heart of patient 26. The tracker module may use any method for location tracking probes known in the art. For example, module 30 may operate a magnetic-field-based location tracking sub-system. (For simplicity, components of such a sub-system are not shown in FIG. 1.) Using tracker module 30, processor 40 is able to measure locations of distal end 32. In addition, using both tracker module 30 and ECG module 36, the processor is able to measure locations of the distal end, as well as LATs of the actual electrical signals detected at these particular locations.

Alternatively or additionally, tracker module 30 may track probe 24 by measuring impedances between electrode 23, electrodes 29, and electrodes 22, as well as the impedances to other electrodes which may be located on the probe. (In this case electrodes 22 and/or electrodes 29 may provide both ECG and location tracking signals.) The Carto3® system, produced by Biosense-Webster (Irvine, Calif.), uses both magnetic field location tracking and impedance measurements for location tracking.

Results of the operations and visualizations performed by processor 40 are presented to physician 28 on a display 48, which typically presents a graphic user interface to the physician, a visual representation of the ECG signals sensed by electrodes 22, and/or an image or map of heart 34 while it is being investigated. In an embodiment, EP activation analysis module 35 presents to the physician a LAT map overlaid with the interpolated ECG amplitude "sails."

The software run by processor 40 may be downloaded to processor 40 in electronic form, over a network, for example, or it may, alternatively or additionally, be provided and/or stored on non-transitory tangible media, such as magnetic, optical, or electronic memory. In particular, processor 40 runs a dedicated algorithm that enables processor 40 to perform the disclosed steps, as described below.

Electrophysiological Ripple Mapping Visualization Method

Figure 2:
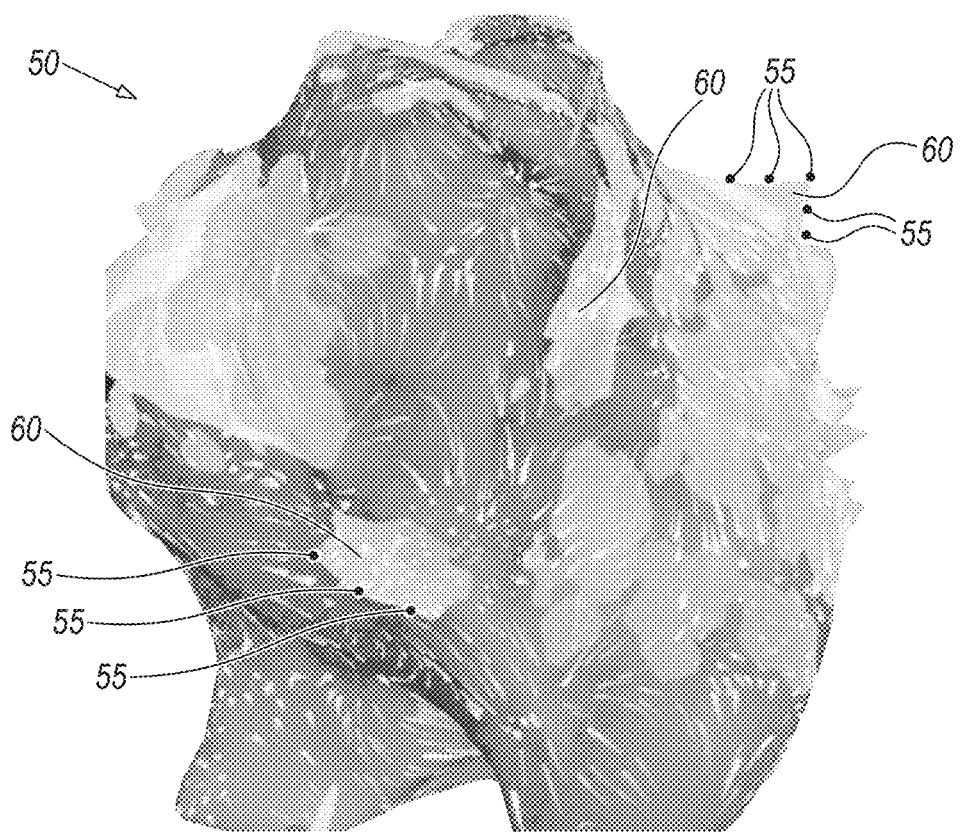
FIG. 2 is a volume rendering showing ripple-mapping visualization of ECG amplitudes overlaid on a cardiac chamber anatomy, in accordance with an embodiment of the present invention.

FIG. 2 is a volume rendering showing ripple-mapping visualization of ECG amplitudes overlaid on a cardiac chamber 50 anatomy, in accordance with an embodiment of the present invention. In FIG. 2, ECG measured values, i.e., spikes 55, are overlaid on a grey-scale anatomical map, where the height of spikes 55 gives a measure of the ECG signal amplitude at the spike positions. As seen, the disclosed visualization method not only gives the value of the ECG spikes at the given position, but also at any intermediate positions, which forms sail 60 shapes of the local ECG amplitudes.

As noted above, to visualize ECG signals as disclosed, processor 40 interpolates values of ECG signals 55 at points near a selected location, and connects the topographical height values above the 3D rendering so as to produce the disclosed continuous ripple visualization. In an embodiment (not shown in FIG. 2), processor 40 generates semi-transparent sails 60 in order not to hide details behind them (i.e., to show details of underlying map).

The example ripple-mapping visualization shown in FIG. 2 is chosen purely for the sake of conceptual clarity. Various additional visualization tools may apply, such a presenting numbers, a magnifying glass effect to view sails 60 in detail, and others.

Figure 3:
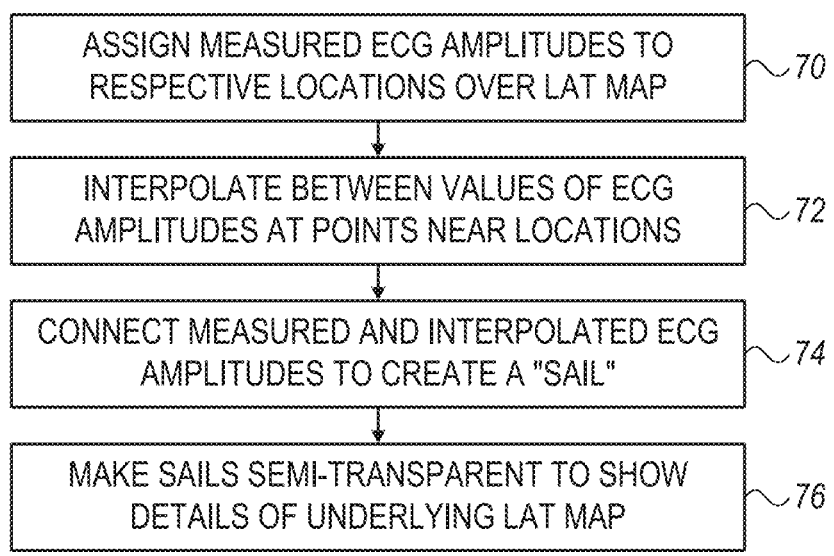
FIG. 3 is flow chart that schematically illustrates a method and algorithm for ripple-mapping visualization of ECG amplitudes shown in FIG. 2, in accordance with an embodiment of the present invention.

FIG. 3 is flow chart that schematically illustrates a method for ripple-mapping visualization of ECG amplitudes shown in FIG. 2, in accordance with an embodiment of the present invention. The algorithm, according to the presented embodiment, carries out a process that begins with processor 40 assigning measured ECG amplitudes 55 to respective locations over an anatomical map of a cardiac chamber (i.e., overlaid on the electro-anatomically—such as LAT—mapped surface of chamber 50), at an ECG amplitude assigning step 70.

Next, at interpolation step 72, processor 40 interpolates over values of ECG at points near each location. Next, at each location, processor 40 connects measured and interpolated ECG amplitudes to create sails 60, at an interconnecting ECG amplitudes step 74. In an embodiment, processor 40 further makes sails 60 semi-transparent, at a sail visualization step 76. Processor 40 presents the resulting visualization (LAT map with overlaid interpolated ECG amplitudes) to physician 28 on display 48.

The example flow chart shown in FIG. 3 is chosen purely for the sake of conceptual clarity. The present embodiment also comprises additional steps of the algorithm. Examples include additional visualizations, such as conduction arrows between and under sails 60. Such additional steps have been omitted from the disclosure herein purposely on order to provide a more simplified flow chart.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for ripple-mapping visualization of cardiac electrophysiological maps, the method comprising:
   generating, via a processor and a catheter inserted into a heart of a patient, an anatomical map of at least a portion of the heart;
   assigning, via the processor, measured ECG signal amplitudes to respective locations over at least a region of the anatomical map of the heart;
   interpolating, via the processor, the ECG signal amplitudes at points near the respective locations;
   connecting, via the processor, the measured and interpolated ECG amplitudes to create surface representation sails having a continuous ripple; and
   presenting on a display and via the processor, the surface representation sails overlaid on the anatomical map for enhanced visualization and diagnostic value of cardiac electrophysiological maps.

2. The method according to claim 1, wherein presenting the surface representation comprises visualizing respective values of the surface representation as topographical heights above the anatomical map.

3. The method according to claim 1, wherein presenting the surface representation comprises presenting a semi-transparent surface that retains the anatomical map visible.

4. The method according to claim 1, wherein interpolating the ECG signal amplitudes comprises forming a shape comprising the interpolated and measured ECG amplitude values.

5. The method according to claim 1, wherein the anatomical map presents Local Activation Times (LAT).

6. A system for ripple-mapping visualization of cardiac electrophysiological maps, the system comprising:
   a memory, which is configured to:
      store an anatomical map of at least a portion of a heart; and
      store, for at least a region of the anatomical map, positions and respective electrocardiogram (ECG) signal amplitudes measured, via a catheter, at the respective positions; and
   a processor, which is configured to:
      interpolate the ECG signal amplitudes at points near the respective positions;
      connect the measured and interpolated ECG amplitudes to create surface representation sails having a continuous ripple; and
      present the surface representation sails overlaid on the anatomical map for enhanced visualization and diagnostic value of cardiac electrophysiological maps.

7. The system according to claim 6, wherein the processor is configured to present the surface representation by visualizing respective values of the surface representation as topographical heights above the anatomical map.

8. The system according to claim 6, wherein the processor is configured to present the surface representation by presenting a semi-transparent surface that retains the anatomical map visible.

9. The system according to claim 6, wherein the processor is configured to interpolate the ECG signal amplitudes by forming a shape comprising the interpolated and measured ECG amplitude values.

10. The system according to claim 6, wherein the anatomical map presents Local Activation Times (LAT).

* * * * *